United States Patent [19]
Trygstad

[11] Patent Number: 5,936,727
[45] Date of Patent: *Aug. 10, 1999

[54] WAVELENGTH STANDARD

[75] Inventor: W. Marcus Trygstad, Ellicott City, Md.

[73] Assignee: Foss NIRSystems, Inc., Silver Spring, Md.

[*] Notice: This patent issued on a continued prosecution application filed under 37 CFR 1.53(d), and is subject to the twenty year patent term provisions of 35 U.S.C. 154(a)(2).

[21] Appl. No.: 08/842,260

[22] Filed: Apr. 24, 1997

[51] Int. Cl.$^6$ .................................................... G01J 1/02
[52] U.S. Cl. ..................................... 356/243.5; 356/243.1
[58] Field of Search ............................... 356/243, 243.1, 356/243.5; 250/252.1

[56] References Cited

U.S. PATENT DOCUMENTS

| | | |
|---|---|---|
| 4,461,718 | 7/1984 | Kaye et al. ........................... 250/252.1 |
| 4,647,198 | 3/1987 | Sommer . |
| 4,761,552 | 8/1988 | Rosenthal ............................. 250/252.1 |
| 4,836,673 | 6/1989 | Esquivel .................................. 356/243 |
| 4,886,965 | 12/1989 | Esquivel .................................. 356/243 |
| 4,912,720 | 3/1990 | Springsteen . |
| 5,462,705 | 10/1995 | Springsteen . |
| 5,488,473 | 1/1996 | Springsteen et al. . |
| 5,537,203 | 7/1996 | Carr . |
| 5,596,450 | 1/1997 | Hannon et al. . |
| 5,689,364 | 11/1997 | McGregor et al. . |

OTHER PUBLICATIONS

Victor R. Weidner and Jack J. Hsia, Reflection Properties of Pressed Polytetrafluoroethylene Powder J. Opt. Soc. Am/vol. 71, No. 7/Jul. 1981, pp. 856–861.

Victor R. Weidner, Patricia Y. Barnes, and Kenneth Eckerle, A Wavelength Standard for the Near Infrared Based on the Reflectance of Rare–Earth Oxides, Journal of Research of the National Bureau of Standards vol. 91, No. 5, Sept.–Oct. 1986, pp. 243–253.

Primary Examiner—Robert H. Kim
Assistant Examiner—Zandia V. Smith
Attorney, Agent, or Firm—Lane, Aitken & McCann

[57] ABSTRACT

In an optical wavelength standard, a concrete matrix embeds wavelength reference material. The concrete matrix is formed from a powdered halogenated polymer (e.g., PTFE) which is mixed with powdered wavelength reference materials, such as rare earth oxides, and the mixture is subjected to sufficient pressure to cause the particles of the halogenated polymer to coalesce into the concrete matrix.

20 Claims, 1 Drawing Sheet

WAVELENGTH STANDARD

This invention relates to a wavelength standard in the visible and infrared spectrum for use in the analysis and identification of materials.

Instruments measuring optical absorbance have proved to be a valuable tool in analyzing materials, both to determine and measure the constituents of materials and to determine and measure properties of materials as well as to identify unknown materials. For these purposes the measurements have been made primarily in the near infrared range, but measurements in the lower end of the visible spectrum have also been used.

A typical near infrared absorbance measuring instrument irradiates the material with near infrared light and detects the near infrared light reflected from or transmitted through the material being analyzed while the wavelength of the near infrared light is restricted to a narrow band, which is varied over the near infrared spectrum. In order to make an accurate analysis or identification of the material, there is a need to have the instrument calibrated so that the wavelengths at which the absorbance measurements are made are precisely identified. In this connection, the National Bureau of Standards developed a reference material which would serve as a wavelength standard in the near infrared range. This reference material was a mixture of three rare earth oxide powders in equal parts by weight, dysprosium oxide, erbium oxide and holmium oxide. This reference material exhibits peaks of absorbance at accurately known wavelengths as described in an article by V. R. Weidner, P. Y. Barnes and K. L. Eckerle entitled "A Wavelength Standard for the Near Infrared Based on the Reflectance of Rare-Earth Oxides" in *Journal of Research of the National Bureau of Standards,* September–October 1986. This rare earth oxide mixture is currently used as a standard by being sealed in a sample cup with a quartz window to permit an absorbance spectrum to be measured with a near infrared spectrophotometer. To serve as a standard, the absorbance peaks exhibited by the standard material must be within plus or minus 1.0 nanometers of the absorbance peaks described in the 1986 article. The mixture of rare earth oxides sealed in a cup with a quartz window meets this tolerance requirement.

However, the standard consisting of the mixture of the rare earth oxide powders has several drawbacks. The powdered material is difficult to pack evenly and tightly in a sample cup such that the material does not shift within the cup and exhibits cracks or voids which are visible through the quartz window. Such voids can shift around thereby physically changing the reference material scanned by the spectrophotometer. While the positions of the absorbance peaks do not change as the voids change position under the window, the intensities of the peaks can and do vary. Moreover, the mechanical properties of the material creates an appearance of an instability in the material. In addition, since the mixture of powder is heterogeneous, there is no assurance that the different powders will not separate or stratify. If local variations in the concentrations are very small, only the intensities in the absorbance peaks measured by the NIR spectrophotometer would change. However, apparent peak positions could change if local proportions of the rare earth oxide powders change significantly. In addition, the material cannot be easily sandwiched as a thin mechanically stable layer between two quartz windows to enable it to be used as a wavelength standard in the transmission mode. To solve the above-described problems in using rare earth oxide powders as a standard, it was once proposed to incorporate the rare earth oxides in a sintered matrix of polytetrafluoroethylene (PTFE) or other perhalopolyethylenes. To make the product, the rare earth powder was mixed with PTFE powder and the resulting mixture was heated to sinter the PTFE particles to embed the rare earth powder in a concrete PTFE matrix. However, when rare earth oxides are incorporated into a thermally sintered matrix of PTFE, the wavelengths of the absorbance peaks exhibited by the sintered material are different from the wavelengths of the absorbance peaks exhibited by the rare earth oxides in powdered form, evidencing that a chemical change occurs during sintering. The peak changes are quite drastic and, as a result, a standard comprising a combination of rare earth oxide power in a thermally sintered matrix is much less useful than it would be if the absorbance peaks matched those of the National Bureau of Standards article.

SUMMARY OF THE PRESENT INVENTION

In accordance with the present invention, a concrete matrix is provided embedding the rare earth oxides uniformly distributed in the matrix and in which the absorbance peaks are in the same wavelength position as in the mixture of the rare earth powders. The absorbance peaks in the resulting material are not changed or shifted by more than one nanometer which is within the tolerance specified in the National Bureau of Standards paper. The word "concrete" as used herein corresponds to its dictionary definition and means "formed by a coalition of particles into one solid mass". The rare earth oxides are embedded in the concrete matrix by mixing the powdered rare earth oxides or other wavelength reference material with powdered matrix material, such as PTFE, and subjecting the mixture to sufficient pressure at ambient temperature to coalesce the matrix material particles into a concrete matrix. When sufficient pressure is applied to the PTFE powder mixed with the rare earth oxides, the particles of PTFE coalese into a concrete cake which holds the particles of rare earth powder immovable within the PTFE matrix. For a reflectance standard, the percentage of rare earth powder would normally be in the range of 5 to 30 percent. Above 33 percent, the cake of PTFE and rare earth oxide becomes too friable. A reflectance standard will normally have a thickness of 10 to 3 millimeters.

In accordance with an alternative embodiment, a transmission standard is provided wherein the PTFE matrix containing the rare earth oxide powder is formed into a thin sheet from 0.3 millimeters to three millimeters thick with a percentage of rare oxide powder of 10 percent to 1 percent by weight.

BRIEF DESCRIPTION OF THE DRAWINGS

The single FIGURE of the drawings schematically illustrates an instrument for analyzing material from its reflectance or transmittance in the near infrared and visible range.

DESCRIPTION OF A PREFERRED EMBODIMENT

Figure 1:
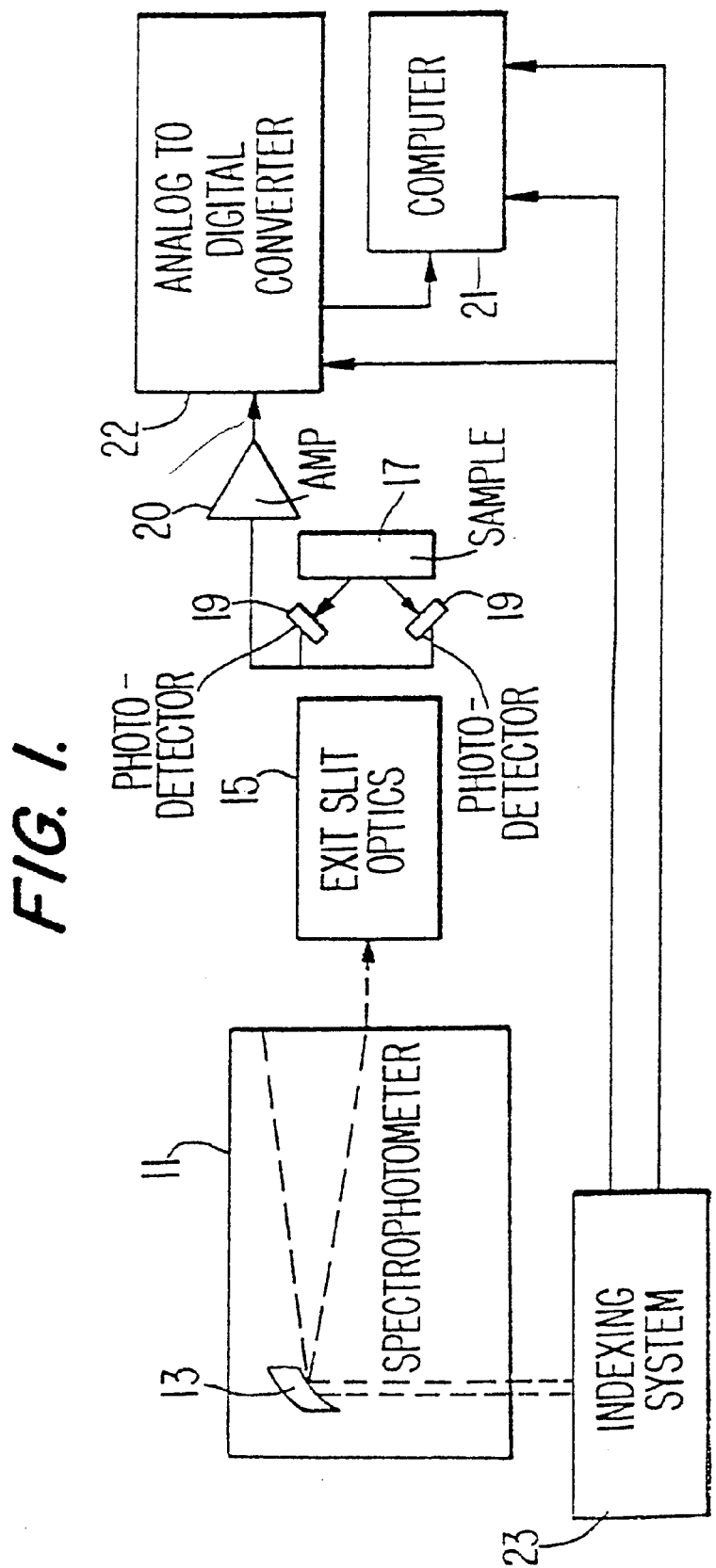

The present invention in a first embodiment is a reflectance standard and in a second embodiment is a transmittance standard both for use in an instrument like that shown in the drawing.

As shown in the drawing, the instrument employed in the system of the present invention comprises a near infrared spectrophotometer 11 having an oscillating grating 13 on which the spectrophotometer directs light. The grating 13 reflects light with a narrow wavelength band through exit slit optics 15 to a sample 17. As the grating oscillates, the center wavelength of the light that irradiates the sample is swept through the near infrared spectrum. Light from the diffraction grating that is reflected by the sample is detected by infrared photodetectors 19. The photodetectors generate a signal that is transmitted to an analog-to-digital converter 22 by amplifier 20. An indexing system 23 generates pulses as the grating 13 oscillates and applies these pulses to a computer 21 and to the analog-to-digital converter 22. In response to the pulses from the indexing system 23, the analog-to-digital converter converts successive samples of the output signal of the amplifier 20 to digital values. Each digital value thus corresponds to the reflectivity of the sample at a specific wavelength in the near infrared range. The computer 21 monitors the angular position of the grating 13 and accordingly monitors the wavelength irradiating the sample as the grating oscillates, by counting the pulses produced by the indexing system 23. The pulses produced by the indexing system 23 define incremental index points at which values of the output signal of the amplifier are converted to digital values. The index points are distributed incrementally throughout the near infrared spectrum and each correspond to a different wavelength at which the sample is irradiated. The computer 21 converts each reflectivity value to an absorbance of the material at the corresponding wavelength. When the transmissivity of the sample is measured, photodetectors will be positioned to receive light transmitted through a sample positioned in the path of the narrow band width light passing through the exit slit optics. The structure and operation of a spectrophotometer is described in greater detail in U.S. Pat. No. 4,969,739.

The accuracy of the instrument in analyzing and identifying materials depends upon the accuracy with which the wavelengths transmitted through the exit slit optics 15 is known. Moreover, the very capability of the instrument to measure some properties of materials is dependent upon this accuracy. For this reason, there is a need to verify with precision that the calibration of the instrument is correct for the wavelengths transmitted through the exit slit optics. Reflectance and transmittance standards, by exhibiting peaks of absorbance at known wavelengths, provide a means to achieve the needed wavelength calibration verification of spectrophotometers. In use, a reflectance standard is positioned in place of the sample 17 to reflect the light transmitted through the exit slit optics to the photodetectors 19 and the spectrograph of the standard is measured. From the spectrograph, the absorbance peaks exhibited by the reflectance standard are detected. This information thus provides a basis for verifying that the wavelengths transmitted through the exit slit optics are correctly and precisely calibrated.

When the spectrophotometer is used to analyze a sample by transmittance through the sample, it is preferable to verify the instrument calibration with a transmittance standard which is positioned in the path of the light passing through the exit slit optics so that the photodetectors will receive light transmitted through the transmittance standard. The transmittance spectrograph is then measured and is used to verify that the wavelength calibration of the instrument is precisely accurate.

The spectrographics measured from the wavelength standards by the spectrophotometer can also be used to actively calibrate the wavelengths transmitted through the exit slit optics of the spectrophotometer at each angular increment of the grating 13. The spectrograph measured from the reflectance standard as descried above provides a basis for actively calibrating the spectrophotometer operating in a reflectance mode and the spectrograph measured from a transmittance standard as described above provides a basis for actively calibrating the spectrophotometer operating in a transmittance mode.

In accordance with the preferred embodiments of the reflectance standard and of the transmittance standard of the present invention, rare earth oxides, dysprosium oxide, erbium oxide and holmium oxide, in a ratio of 1:1:1 by weight are mixed with powdered PTFE. In the reflectance standard, the rare earth oxides are from about 5 to 30 percent by weight of the PTFE powder. In the transmittance standard, the rare earth oxides are from 1 to 10 percent by weight of the PTFE powder. The mixing is carried out to thoroughly blend the rare earth oxide powder in a heterogeneous mixture with the PTFE powder and the resulting mixture is then placed in a die, pressure mold, or between platens, and sufficient pressure (500 to 5,000 pounds per square inch) is applied to the powder mixture to coalese the powdered mixture into a concrete cake at ambient temperature. The resulting cake when analyzed by the instrument of FIG. 1 will exhibit absorbance peaks at the same wavelengths that absorbance peaks are detected from the powder mixture alone, as described in the National Bureau of Standards 1986 paper. The wavelengths are determined to coincide with those of the National Bureau of Standards paper within a tolerance of plus or minus one nanometer which is the accuracy tolerance specified in the National Bureau of Standards paper. It is not critical that the pressure be applied at ambient temperature, but the temperature must be low enough that the absorbance peaks exhibited by the rare earth oxides do not shift when embedded in the concrete PTFE matrix. The temperature should be low enough so that the particles of the PTFE powder coalesce due to the applied pressure rather than from the surface melting of the PTFE particles.

When the material is to be used as a reflectance standard, it will be formed into a concrete block at least three millimeters thick and will be formed from a mixture of about 5–30 percent of rare earth oxides by weight to the PTFE powder. When the reference standard is 3 millimeters thick, the preferred percentage of rare earth oxides is 30 percent by weight of the PTFE. When the thickness of the block is 10 millimeters, the preferred percentage of the rare earth oxide in the block is about 5 percent by weight.

The maximum ratio of rare earth oxides to PTFE is about one-third by weight because when the amount of powder substantially exceeds one-third, the resulting cake becomes too friable.

For the transmission standard, the matrix is in the form of a thin sheet from 0.3 millimeters to 3 millimeters thick and the percentage of the rare earth oxides in the material is in the range between 10 percent to 1 percent by weight. In a preferred embodiment of a transmittance standard having a thickness of 0.3 millimeters, the preferred percentage of rare earth oxides to PTFE by weight is 10 percent. In another preferred embodiment of a transmission standard having a thickness of 3 millimeters, the percentage of the rare earth oxides by weight to the PTFE is 1 percent. Generally, for both the transmission standard and the reflectance standard, the thinner the matrix, the greater should be the percentage of rare earth oxide.

Because the National Bureau of Standards paper establishes the three rare earth oxides in the 1:1:1 ratio by weight as an absorbance reflectance standard for wavelength calibration, the preferred rare earth oxide powders in the present invention are these same three rare earth oxide powders and in this same ratio. However, one or two of the three rare earth oxide powders can be omitted from the cake and the resulting product will still be an effective reflectance standard. In addition, the ratios of powder can be varied to achieve a range of selected relative intensities. In each case, the rare earth oxide powder material will exhibit absorptive peaks in the matrix at the same wavelengths that the material exhibits in powder form.

In addition, other rare earth oxides may be used besides those specified in the National Bureau of Standards paper. In accordance with the invention, oxides of any of the series of 15 metallic elements having atomic numbers ranging from 57 to 71 may be used. This group consists of lanthanum, cerium, praseodymium, neodymium, promethium, samarium, europium, gadolinium, terbium, dysprosium, holmium, erbium, thulium, yttervium and lutetium. Another material which may be used as the wavelength reference material is talc ($Mg_3Si_4O_{10}(OH)_2$). Talc exhibits few absorbance peaks, but the peaks are extraordinarily narrow, which makes a reference standard using talc as the wavelength reference material useful in evaluating the bandwidth of the instrument.

Another way of embedding the rare earth oxide materials in the matrix is to dope the rare earth oxides into glass which is then ground and compressed in the matrix as described above. Rare earth oxides doped in glass can be used as a transmission standard, but they will not exhibit the same absorption peaks that they exhibit in pure or powder form. When glass containing rare earth oxides is ground and then is embedded in a PTFE matrix or its equivalent and the matrix is shaped to be a reflectance standard, the resulting reflectance standard will exhibit the same peaks of absorbance that the transmission standard of glass doped with the rare earth oxides exhibits.

Alternatively, other materials which exhibit absorbance peaks in the near infrared and visible spectrum may also be used. For example, powdered polystyrene or powdered polyethylene can be mixed with powdered PTFE to take advantage of the reflectance properties of PTFE as a matrix embedding the powdered polystyrene or polyethylene. Such a product allows control of all variables to optimize a standard for a given application. In addition, polystyrene or polyethylene may be blended with minerals or rare earth materials as well.

As described above, the preferred matrix material which embeds the powdered wavelength reference material is PTFE. PTFE is the preferred material for the matrix because it has absorbances which are well characterized in reflectance. The absorbance features of PTFE are very broad and very weak and PTFE lacks absorbance peaks characteristic of wavelength reference materials. The strongest absorbances which might interfere with peaks and reference materials only occur at longer wavelengths leaving most of the NIR and the visible spectrum free from interference. The PTFE material, besides having low absorbance, is highly scattering in the optical sense. This characteristic gives the material high reflectance. Moreover, light penetrating in the material scatters internally and if the material is thin enough, the light is transmitted through the material. The PTFE may be thought of as a diluent and a glue which holds the wavelength reference material in place and optical properties of which permit it to reflect or transmit light with practically no absorption of visible or near infrared light while permitting the light to interact with materials embedded in the matrix. While the PTFE is a preferred material for the reasons given above, other materials may be used for the matrix. Specifically, any perhalopolyethylene may be used, such as poly(perchlorethylene) or poly(per(chlorofluoro)ethylene) or poly(chlorotrifluorethylene) may be used. As another variation a monomer, per(chlorofluoro)ethylene, can be copolymerized with tetrafluorethylene to provide the powder from which the matrix is formed.

Generally, any solid polymeric material that contains no bonds between hydrogen and carbon, oxygen or nitrogen, would provide a matrix which would be highly suitable substitute for PTFE. In such a polymer, the backbone of the polymer chain contains only carbon. However, it is possible for the polymer chain to include other atoms such as oxygen as long as the oxygen or other atom is bonded only to carbon and is not bonded to any other element such as hydrogen. Examples of such materials based on tetrafluorethylene oxide and perfluorethylene oxide are: poly(tetrafluorethylene oxide-co-difluoromethylene oxide); poly(tetrafluorethylene-co-tetrafluoroethylene perfluoropropyl ether); and poly(perfluoropropylene oxide-co-perfluoroformaldehyde).

Many halogenated polymers exist which are related to those described above, but which are not perhalogenated. Such polymers, called hydrohalo polymers, can be prepared from monomers which contain some hydrogen as well as halogen, e.g., vinylidene chloride, $CH_2Cl_2$, or vinylidene fluoride, $CH_2CF_2$. Alternatively, hydrohalo polymers can be prepared through copolymerization of monomers containing no halogen, such as ethylene, and monomers that are perhalogenated, such as tetrafluorethylene. Such compounds would be sparsely populated with CH bonds which will absorb in the infrared and near infrared range, but the absorptivities of such materials are reduced compared to those in their pure hydrocarbon counterparts due to the effects caused by the presence of flourine or simply dilution. While such compounds have significantly stronger absorbances than PTFE, they nevertheless could be useful as a matrix material. For such compounds to have a practical utility as a matrix in a reference standard, the frequency of occurrence of the C—H bonds in the material must be low enough that at least half of the absorbance peaks caused by the wavelength reference material in the matrix remain substantially unshifted in wavelength and unobscured.

The above description is of preferred embodiments of the invention and modifications can be made thereto without departing from the spirit and scope of the invention, as defined in the appended claims.

I claim:

1. A wavelength standard for the visible and near infrared spectrum comprising a concrete matrix having distributed in said matrix and embedded in the matrix a wavelength reference material which exhibits peaks of radiation absorbance at known wavelengths in the visible or infrared spectrum, said matrix being formed by mixing a polymeric particulate material with a wavelength reference material to form a mixture of said polymeric material and said wavelength reference material and subjecting said mixture to sufficient pressure to cause the particles of said polymeric material coalesce into said concrete matrix embedding said wavelength reference material in said matrix, said polymeric material comprising a halogenated polymer in which the frequency of occurrence of C—H bonds in said polymeric material is sufficiently low so that at last half of the absorbance peaks of said wavelength reference material remain substantially unshifted or obscured, said concrete matrix with said wavelength reference material embedded therein exhibiting absorbance peaks at the same wavelength as said wavelength reference material.

2. A wavelength standard as recited in claim 1, wherein said polymeric material is PTFE.

3. A wavelength standard as recited in claim 2, wherein said wavelength reference material comprises at least one rare earth oxide.

4. A wavelength standard as recited in claim 2, wherein said wavelength reference material comprises a mixture of a plurality of rare earth oxides.

5. A wavelength standard as recited in claim 2, wherein said wavelength reference material comprises one or more rare earth oxides selected from the group consisting of dysprosium, erbium and holmium.

6. A wavelength standard as recited in claim 5, wherein said wavelength reference material consists of oxides of dysprosium, erbium an holmium in a proportion of 1:1:1 by weight.

7. A wavelength standard as recited in claim 2, wherein said wavelength reference material comprises talc.

8. A wavelength standard as recited in claim 2, wherein said wavelength reference material comprises polystyrene.

9. A wavelength standard as recited in claim 2, wherein said wavelength reference material comprises polyethylene.

10. A wavelength standard as recited in claim 1, wherein said wavelength reference material comprises at least one rare earth oxide.

11. A wavelength standard as recited in claim 1, wherein said wavelength reference material consists of a mixture of a plurality of rare earth oxides.

12. A wavelength standard as recited in claim 1, wherein said wavelength reference material comprises one or more rare earth oxides selected from the group consisting of dysprosium, erbium and holmium.

13. A wavelength standard as recited in claim 1, wherein said wavelength reference material comprises talc.

14. A wavelength standard as recited in claim 1, wherein said wavelength reference material comprises polystyrene.

15. A wavelength standard as recited in claim 1, wherein said wavelength reference material comprises polyethylene.

16. A wavelength standard as recited in claim 1, wherein said polymeric material contains essentially no C—H bonds.

17. A wavelength standard as recited in claim 1, wherein said polymeric material consists essentially of a perhalopolyethylene.

18. A wavelength standard as recited in claim 17, wherein said wavelength reference material comprises at least one rare earth oxide.

19. A wavelength standard as recited in claim 17, wherein said wavelength reference material comprises one or more rare earth oxides selected from the group consisting of dysprosium, erbium and holmium.

20. A wavelength standard as recited in claim 17, wherein said wavelength reference material comprises talc.

* * * * *